(12) United States Patent
Henderson et al.

(10) Patent No.: US 6,450,922 B1
(45) Date of Patent: Sep. 17, 2002

(54) ELECTRONIC EXERCISE SYSTEM

(75) Inventors: Scott J. Henderson, Los Angeles, CA (US); Tyler C. Marthaler; Jeffrey Q. Nichols, both of New York, NY (US)

(73) Assignee: Graber Products, Inc., Madison, WI (US)

( * ) Notice: Subject to any disclaimer, the term of this patent is extended or adjusted under 35 U.S.C. 154(b) by 0 days.

(21) Appl. No.: 09/182,977

(22) Filed: Oct. 29, 1998

(Under 37 CFR 1.47)

Related U.S. Application Data

(63) Continuation of application No. 09/071,713, filed on May 1, 1998, now abandoned, which is a continuation of application No. 08/887,240, filed on Jul. 2, 1997, now abandoned.
(60) Provisional application No. 60/020,565, filed on Jul. 2, 1996.

(51) Int. Cl.⁷ .............................................. A63B 21/00
(52) U.S. Cl. .................... 482/8; 482/4; 482/9; 482/901
(58) Field of Search ............................ 482/1–9, 51, 54, 482/900–902

(56) References Cited

U.S. PATENT DOCUMENTS

| | | | |
|---|---|---|---|
| 4,828,257 A | | 5/1989 | Dyer et al. |
| 4,907,795 A | * | 3/1990 | Shaw et al. ................ 482/9 |
| 4,925,189 A | | 5/1990 | Braeunig |
| 4,976,424 A | | 12/1990 | Sargeant et al. |
| 5,213,555 A | * | 5/1993 | Hood et al. ................ 482/57 |
| 5,335,188 A | * | 8/1994 | Brisson ..................... 482/8 |
| 5,462,503 A | | 10/1995 | Benjamin et al. ........... 482/4 |
| 5,524,637 A | | 6/1996 | Erickson |
| 5,527,239 A | | 6/1996 | Abbondanza |
| 5,785,631 A | * | 7/1998 | Heidecke .................... 482/5 |
| 5,888,172 A | * | 3/1999 | Andrus et al. .............. 482/7 |
| 5,916,063 A | * | 6/1999 | Alessandri ................. 482/4 |
| 6,024,675 A | * | 2/2000 | Kashiwaguchi ............ 482/4 |

FOREIGN PATENT DOCUMENTS

| | | |
|---|---|---|
| EP | 0841079 | 8/1994 |

* cited by examiner

*Primary Examiner*—Glenn E. Richman
(74) *Attorney, Agent, or Firm*—Boyle, Fredrickson, Newholm, Stein & Gratz, S.C.

(57) ABSTRACT

A physical activity monitor, during a first period, records data characterizing a physical activity by a user, and an exercise device uses the recorded data of the physical activity monitor to simulate the physical activity for the user during a second period.

34 Claims, 18 Drawing Sheets

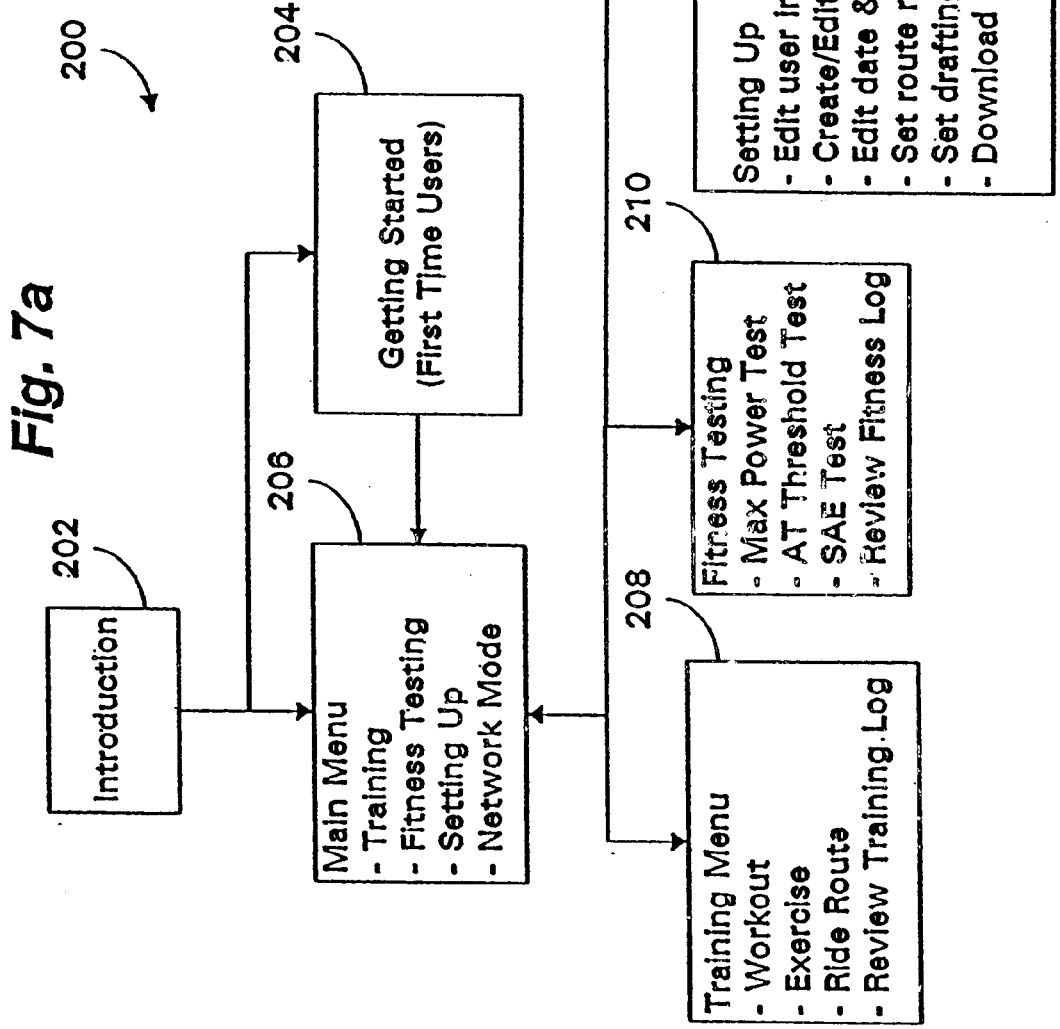

Select a training activity

TRAINING

▲ Workout: Ride today's workout or
   view your schedule
Exercise: Train your Specific
   riding skills
Ride Route: Experience the feel
   of a course
Review Log: Evaluate your training

*Fig. 8b*

FITNESS

Select a test or review
your fitness log

MP Test: Determine your peak output
LT Test: Find your aerobic/anaerobic
threshold
SAE Test: Measure the duration
of your LT output Fitness Log: Review your past
fitness tests

Fig. 8c

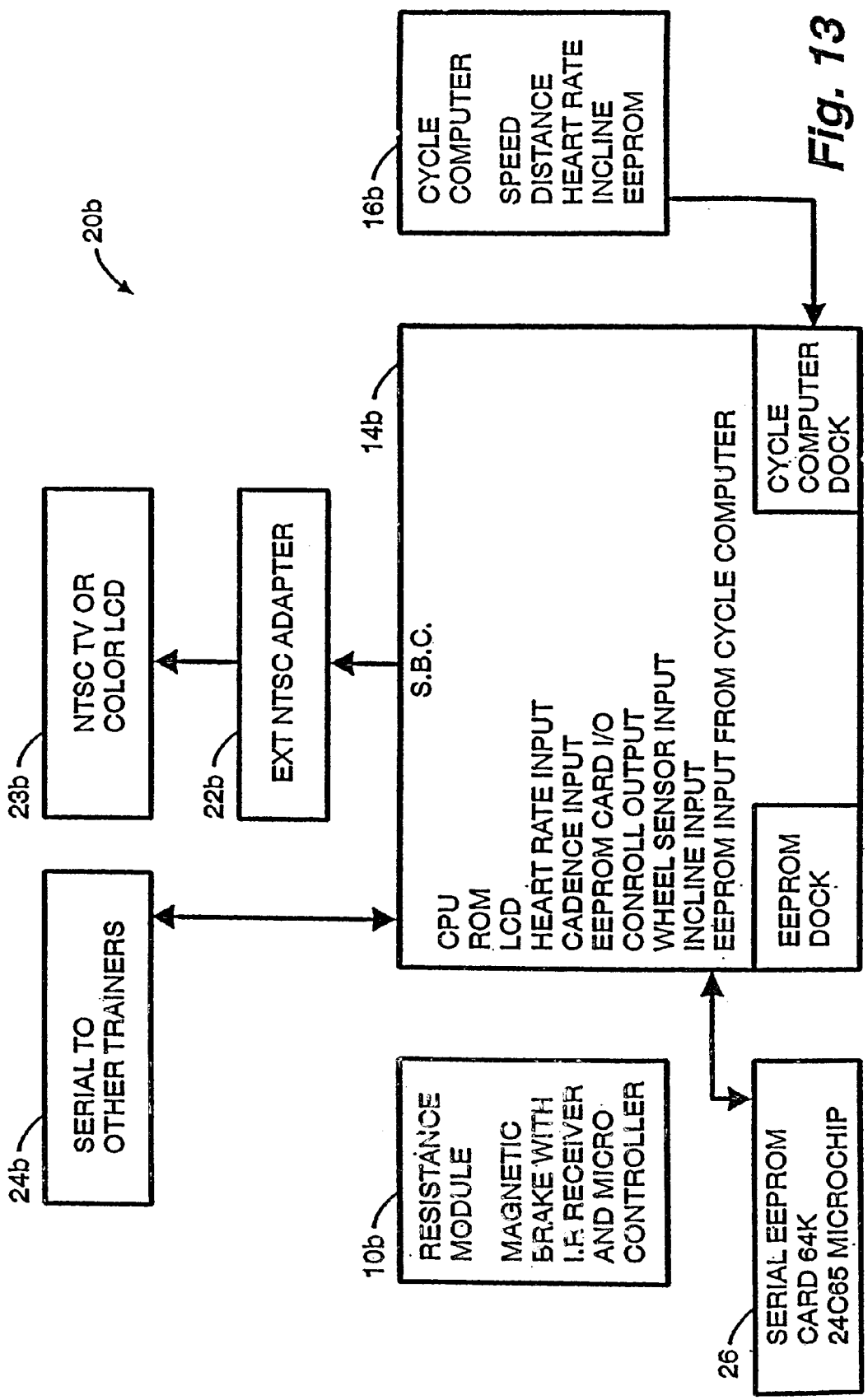

ELECTRONIC EXERCISE SYSTEM

This is a continuation of U.S. application Ser. No. 09/071,713, entitled ELECTRONIC EXERCISE SYSTEM, filed May 1, 1998, now abandoned which is a continuation of U.S. application Ser. No. 08/887,240, filed on Jul. 2, 1997, now abandoned which is a continuation of provisional application No. 60/020,565, filed on Jul. 2, 1996.

BACKGROUND

The present invention relates generally to exercise and to exercise machines or training devices for providing physical exercise for a user.

For many years, bicycle enthusiasts have used bicycle trainers to convert their bicycles for stationary (often indoors) riding. Rather than ride through inclement weather, the cyclist can use the trainer to ride indoors and obtain an aerobic, cardiovascular workout. Bicycle trainers also obviate the need for purchasing a separate stationary bicycle for those persons who want to occasionally workout while, for example, reading or watching television. A bicycle trainer should be easy to use and, to the extent possible, simulate bicycle riding on the open road.

Indoor stationary machines have also been developed or replicating a number of other sports activities, such as running, climbing, skiing, and swimming. Such stationary exercise machines can provide a number of features, including displays of a preset or user-defined course (e.g., a running profile for a stationary treadmill machine), exercise statistics, and measurements of the user's heart rate.

SUMMARY

In general, in one aspect, the invention features a physical activity monitor that during a first period records data characterizing a physical activity by a user, and an exercise device that uses the recorded data of the physical activity monitor to simulate the physical activity for the user during a second period.

Embodiments of the invention may include one or more of the following features. The physical activity monitor can measure a first index of physical exertion. The first index of physical exertion can include an index of a distance traveled by the user, an inclination of the user, an index of a force exerted by the user, and an index of a heart rate of the user. The exercise device can comprise a controller and a resistance provider, the controller being adapted to receive the data recorded by the physical activity monitor and to control the resistance provider in accordance with the received data to simulate the physical activity. The physical activity of the user simulated by the replication device can include a non-stationary bicycle ride, a non-stationary rock climb, a non-stationary swim, and a non-stationary run.

In general, in another aspect, the invention features a physical activity monitor that records sampled data, the data comprising indices of a force exerted by a user and of a distance traveled by the user during a non-stationary bicycle ride by the user and a stationary exercise device that uses the recorded data of the physical activity monitor to simulate the non-stationary bicycle ride.

Embodiments of the invention may include one or more of the following features. The physical activity monitor can include a rotational sensor attached to a bicycle used during the non-stationary bicycle ride, an inclination sensor, or a heart rate sensor coupled to the user. The stationary exercise device can include a resistance unit removably coupled to a bicycle, and a controller, the controller being adapted to receive the data recorded by the physical activity monitor and to control the resistance unit to simulate the non-stationary bicycle ride.

In general, in another aspect, the invention features a physical activity monitor that records sampled data, the data comprising indices of a force exerted by a user and of a distance traveled by the user during a non-stationary bicycle ride by the user, the physical activity monitor further comprising a rotational sensor attached to a bicycle used during the non-stationary bicycle ride, an inclination sensor, and a heart rate sensor coupled to the user, and a stationary exercise device that uses the recorded data of the physical activity monitor to simulate the non-stationary bicycle ride, the stationary exercise device comprising a resistance unit removably coupled to a bicycle, and a controller, the controller adapted to receive the data recorded by the physical activity monitor and to control the resistance unit to simulate the non-stationary bicycle ride.

In general, in another aspect, the invention features a method including the steps of, during a first period, recording data characterizing a physical activity by a user, and, during a second period, using the recorded data to simulate the physical activity for the user.

In general, in another aspect, the invention features a method including the steps of recording sampled data, the data comprising indices of a force exerted by a user and of a distance traveled by the user during a non-stationary bicycle ride by the user, and using the recorded data to simulate the non-stationary bicycle ride.

In general, in another aspect, the invention features a method including the steps of recording sampled data, the data comprising indices of a force exerted by a user, of a distance traveled by the user, of a heart rate of the user, and of an inclination of a first bicycle, and a rotation of a wheel of the first bicycle, during a non-stationary bicycle ride by the user, and receiving the recorded data and controlling a resistance unit removably coupled to a bicycle to simulate the non-stationary bicycle ride.

In general, in another aspect, the invention features a portable monitor with recording capability for recording an activity, wherein the monitor can be operationally coupled with a device for replicating the recorded activity.

In general, in another aspect, the present invention comprises an exercise device, a first sensor for sensing operational parameters of the exercise device, a control interface for interacting with the first sensor and exercise device, and a second sensor for sensing at least a user's heart rate, said second sensor having recording capability and being dockable with the control interface. In other words, the exercise device of the present invention comprises:

(a) a control unit having a processor;
(b) an input device connected to the control unit for providing information related to a route to be simulated on the exercise device;
(b) a resistance unit module operably connected to the control unit;
(c) an output interface operably connected to the control unit;
(d) a heart rate determination apparatus operably connected to the control unit which provides a heart rate value; and
(e) software means operative on the processor for:
  (1) controlling the resistance unit module based on information provided through the input device regarding the route to be simulated;

(2) outputting exercise related information through the output interface, and
(3) monitoring and processing the heart rate values provided to the control unit.

In general, in another aspect, the invention features an indoor stationary bicycle trainer with a computer controlled variable resistance unit, a rear chain stay mounted, wire or wireless RPM (cadence), speed, and incline sensors, a handlebar mounted control/interface panel for use with the stationary trainer, and a wrist watch type heart rate cycle computer with a route recording capacity, wherein the cycle computer may be docked with the control/interface panel.

Embodiments of the inventions may include the following features. The recording can be of an outdoor exercise route and the playing can take place on a computer controlled indoor training device.

In general, in another aspect, the invention features apparatus for customizing the profile of an exercise route to be simulated on an exercise device, wherein the apparatus comprises:

(a) a processor;
(b) an input device operably connected to the processor; and
(c) software means operative on the processor for:
   (1) receiving information regarding the route to be simulated;
   (2) processing the received route information; and
   (3) controlling the exercise devices to implement the route.

Advantages of the invention include the following. An exerciser or user can train for a particular event, and replicate or simulate performing at a particular location remote from an indoor exercise apparatus. A user can simulate, as closely as possible, the experience of performing or exercising at an outdoor location or famous race course while exercising or training indoors on an exercise machine such as a stationary bicycle. A profile of a period of physical exercise can be recorded and played back to replicate the exercise period. The profile can be repeatably played back. A path of efficient workouts can be specified for a user to straightforwardly achieve a fitness goal.

Digital recordings or maps (which may be in the form of a CD-ROM, floppy disk, PCMCIA, EEPROM or the like) can be provided of particular exercise routes, road racing, mountain biking, triathlon courses and the like, and these recordings or maps can provide specific or tailored workouts based on heart rate, power output or other parameters selected in conjunction with a particular exercise route. The invention may be used by persons at any skill or fitness level to train for or attempt a particular race, e.g., a famous marathon. The geographical features of a particular location, i.e., length, the altitude at selected spots, local incline, slope, the local wind resistance, etc., along the race course can be recorded or programmed into a microprocessor/controller and then translated and expressed into resistance levels.

A programmable controller can be adapted to provide a rehabilitative workout wherein the exercise device (e.g., a stationary bicycle) can be powered or driven by a suitable motor or the like to manipulate the limbs of an injured or paralyzed person at a selected level of exertion.

Data for a plurality of outdoor and indoor exercise sessions can be recorded and accumulated. Basic fitness level tests, including anaerobic threshold (AT) tests, power tests and a variety of other exercise test programs can be provided, to test a user's progress and to further revise a prescribed fitness regime. Two or more systems of the present invention can be coupled for providing competition in the same locale, or electronically via a network or on-line service.

These and other features and advantages of the present invention will become more apparent from the following description, drawings, and claims.

DRAWINGS

FIGS. 7a through 7c are flowcharts of user interaction screens for the electronic exercise system.

FIGS. 8a through 8e are representations of user interaction screens for the electronic exercise system.

FIG. 13 is a schematic of an electronic exercise system.

DESCRIPTION

Figure 1:
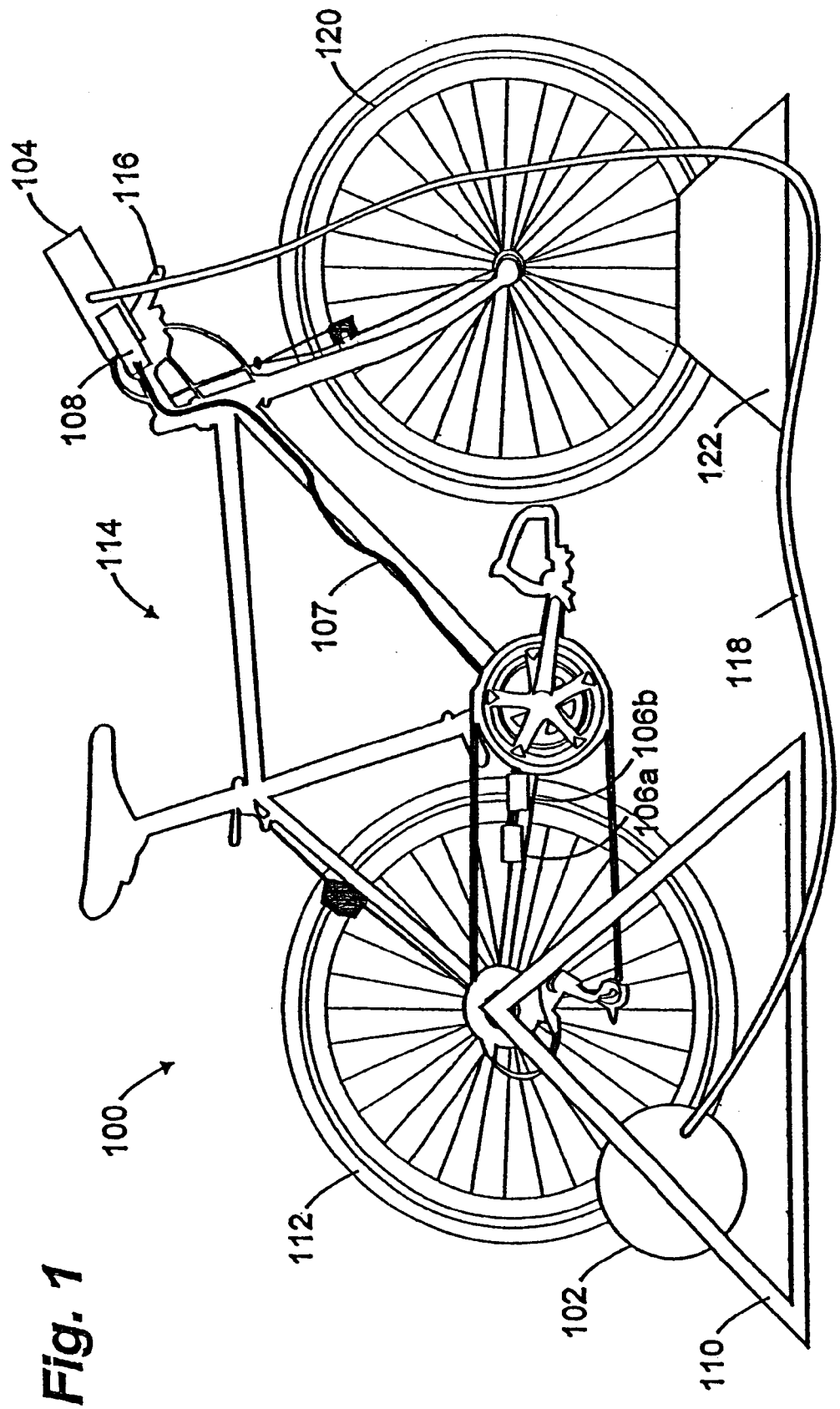
FIG. 1 is a schematic of an electronic exercise system.

Referring to FIG. 1, an electronic exercise system includes resistance unit 102, base controller 104, rear wheel sensor 106a, cadence sensor 106b, and route computer 108. Resistance unit 102 is held in position via frame 110 to removably couple to a rear wheel 112 of a bicycle 114. Base controller 104 removably attaches to handlebars 116 of bicycle 114, and also couples via connector 118 to resistance unit 102. Rear wheel sensor 106a can be located adjacent (or coupled to) rear wheel 112 of bicycle 114 for measuring the wheel's RPM, and cadence sensor 106b, located adjacent the pedal cranks, can measure the cadence of a user's pedal stroke. Sensors 106a and 106b can also be mounted in the same module, and attached at a position adjacent both the rear wheel and pedal cranks. Route computer 108 also attaches to handlebars 116. The front wheel 120 of bicycle 114 can be held properly level with rear wheel 112 via riser block 122. The general structures of a resistance unit held in a frame and a riser block can be found in U.S. Pat. No. 5,611,759, and U.S. provisional patent application Ser. No. 60/027,695, incorporated herein by reference.

Figure 2:
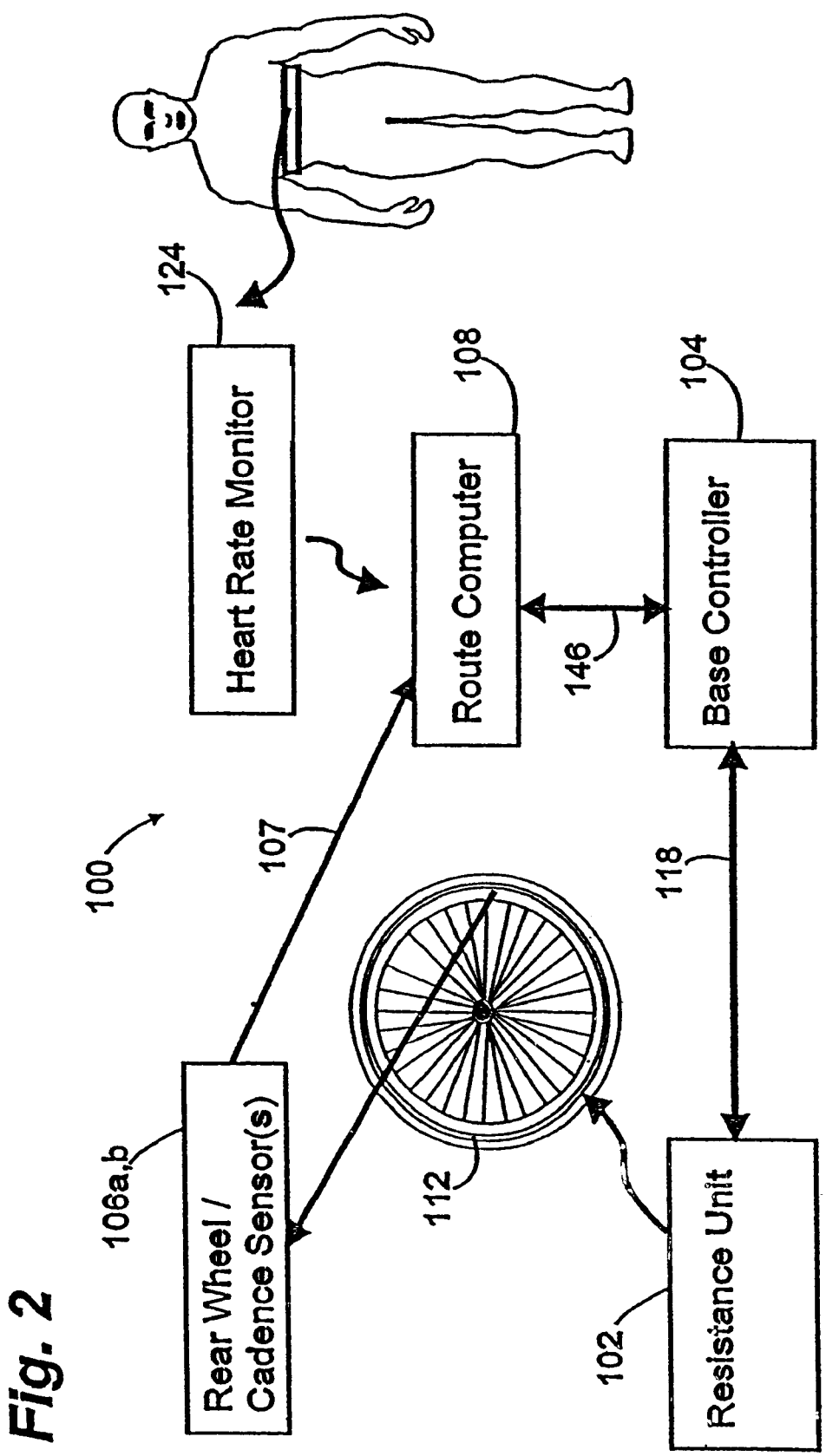
FIG. 2 is a relational diagram of an electronic exercise system.

Referring to FIG. 2, rear wheel sensor 106a and cadence sensor 106b couple to route computer 108 via cable 107, while heart rate monitor 124 (which can be a conventional chest or wrist-type heart rate monitor) communicates via an RF transceiver with route computer 108. When a user exercises with bicycle 114 outdoors, away from base controller 104 and resistance unit 102, route computer 108 monitors and stores information from heart rate monitor 124, rear wheel sensor 106a, and cadence sensor 106b. Route computer 108 starts recording data when cadence sensor 106b or rear wheel sensor 106a senses motion (after the user instructs route computer 108 to record). Route computer 108 stops recording when motion stops, thereby "stitching" together a route despite any number of stops along the way. When the user docks bicycle 114 with resistance unit 102 and base controller 104, route computer 108 attaches to base controller 104 to transfer such stored route information. Route computer 108 automatically resets after each such docking and downloading operation, but also can be manually reset (explained further below) at any time by the user.

Figure 3A:
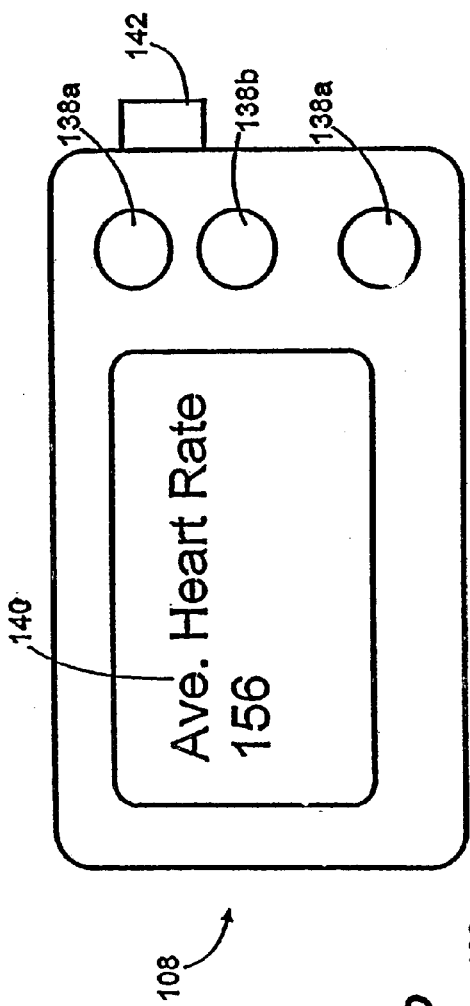
FIGS. 3a and 3b are front and schematic representations of a route computer.
Figure 3B:
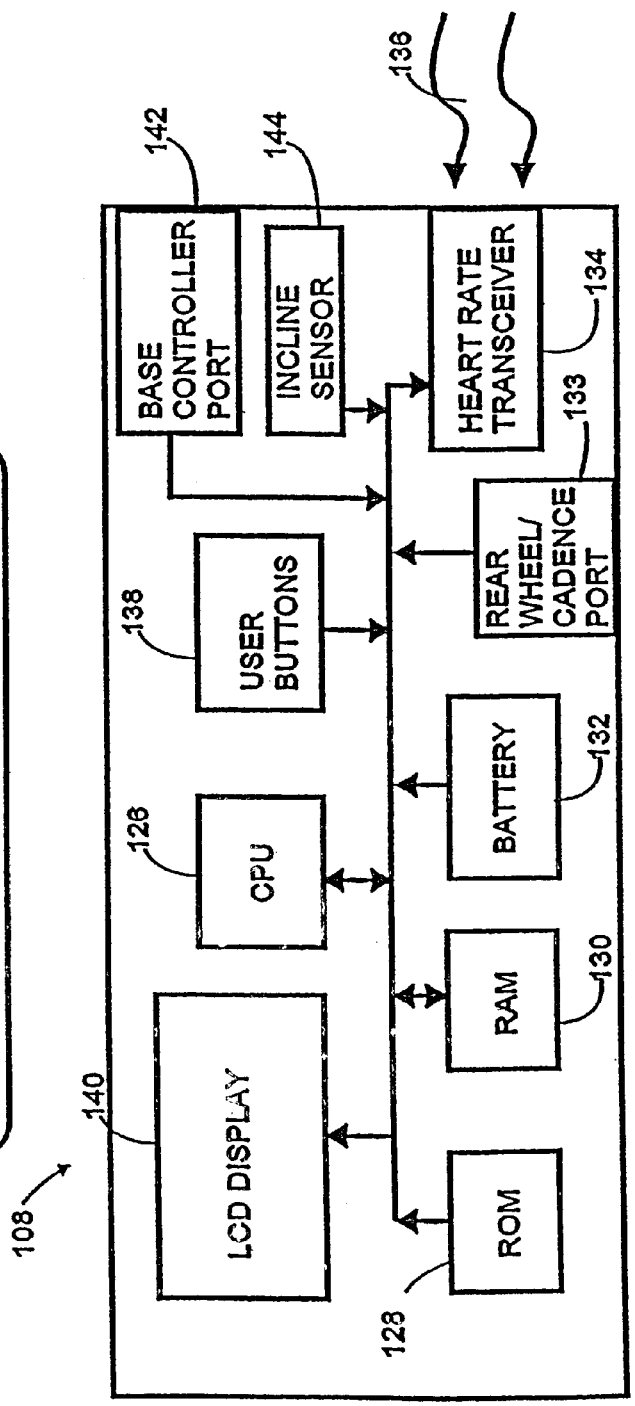

Referring to FIGS. 3a and 3b, route computer 108 includes a microprocessor CPU 126, ROM 128 for storing fixed program information, RAM 130 for storing accumulated route information and temporary program information, battery 132 (or other power source, e.g., solar cell and storage device), rear wheel (or cadence) sensor port 133 for receiving information from rear wheel sensor 106a or cadence sensor 106b, RF transceiver 134 for receiving RF information 136 from heart rate monitor 124, user input buttons 138, LCD (or similar) display 140 for displaying information to the user, base controller port 142 for receiving a connection from base controller 104 when docked, and incline sensor 144 that detects the instantaneous incline of the bicycle at selected intervals.

Algorithms can be employed in route computer 108 (or in base controller 104) to adjust each instantaneous inclination measurement to subtract out the effects of bicycle acceleration, to provide a more accurate inclination measurement. Buttons 138a through 138c can be programmed to be operated separately or together to scroll through various route computer functions. A "start over" button resets the memory of the route computer to record a new route, and sets the current inclination to zero (use of a GPS-type positioning system could allow self-calibration). Various instantaneous and statistical measurements can be displayed to the user, who can scroll through display screens with buttons 138a through 138c. As noted above, route computer 108 can measure the instantaneous speed, user heart rate, incline, cadence and/or RPM of the bicycle wheels, as well as keep track of elapsed distance traveled and maximums and averages of various measurements. These stored averages and statistics can also be reset by specific button press(es).

Incline sensor 144 can be an AU6004 gold contact self-damping fluid inclination sensor, available from Spectron Glass, and is driven by CPU 126 differentially at low frequencies via AC-coupling (to prevent depletion of the leads). Signals measured on the third lead of incline sensor 144 indicate fluid imbalances and therefore inclination changes. Incline sensor has, preferably, a 30 percent range of sensing for incline/grade, imbedded within an overall 45 percent range, allowing 15 percent of the range to allow for variations in the attachment of route computer 108 (with incline sensor 144) relative to handlebar 116 of bicycle 114. By measuring and using the stored local inclinations, electronic exercise system 100 can simulate local difficulties along a particular route (related to the relative local steepness or descent) thereby creating a relatively realistic route simulation.

Figure 4A:
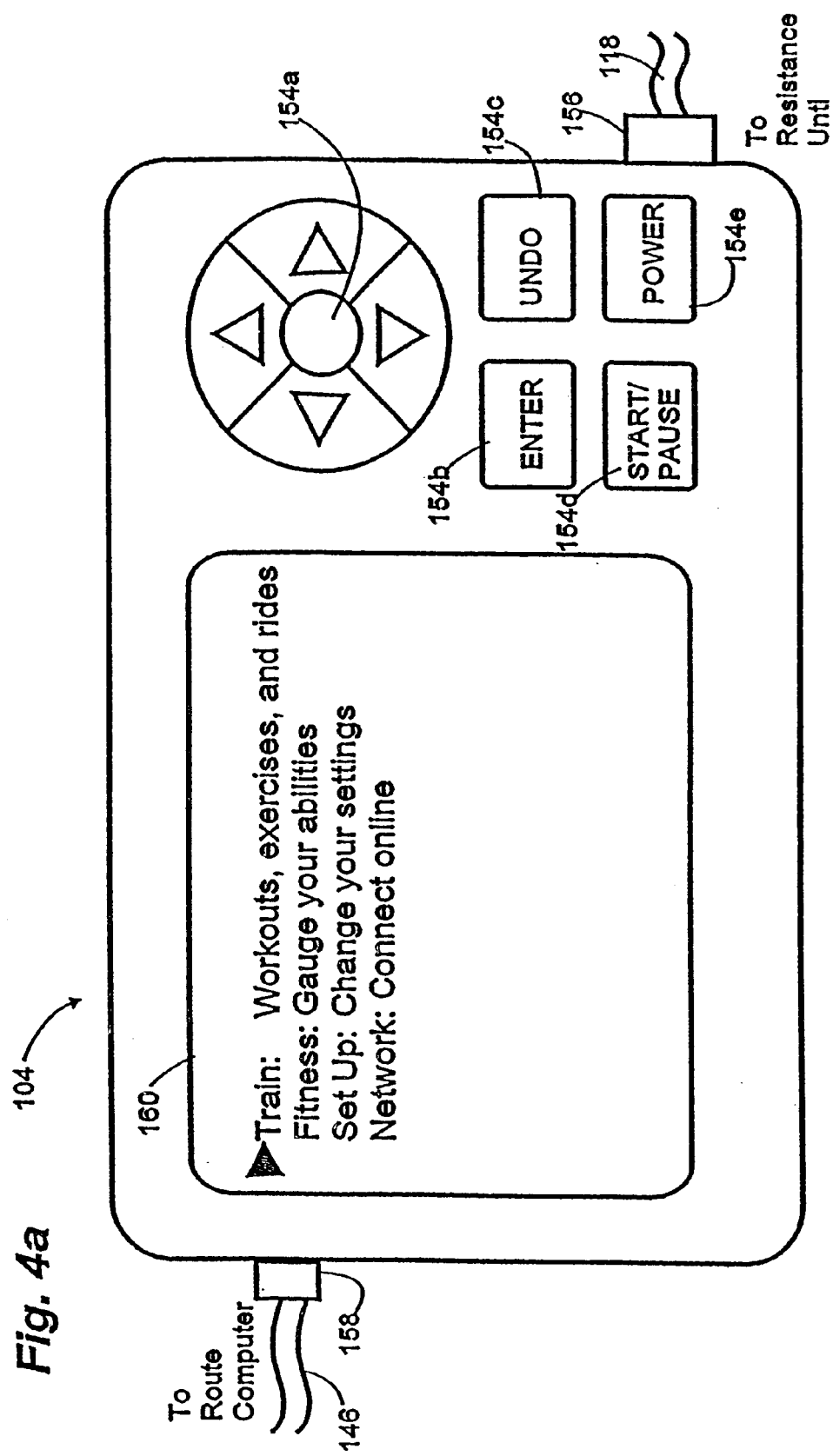
FIGS. 4a and 4b are front and schematic representations of a base controller.
Figure 4B:
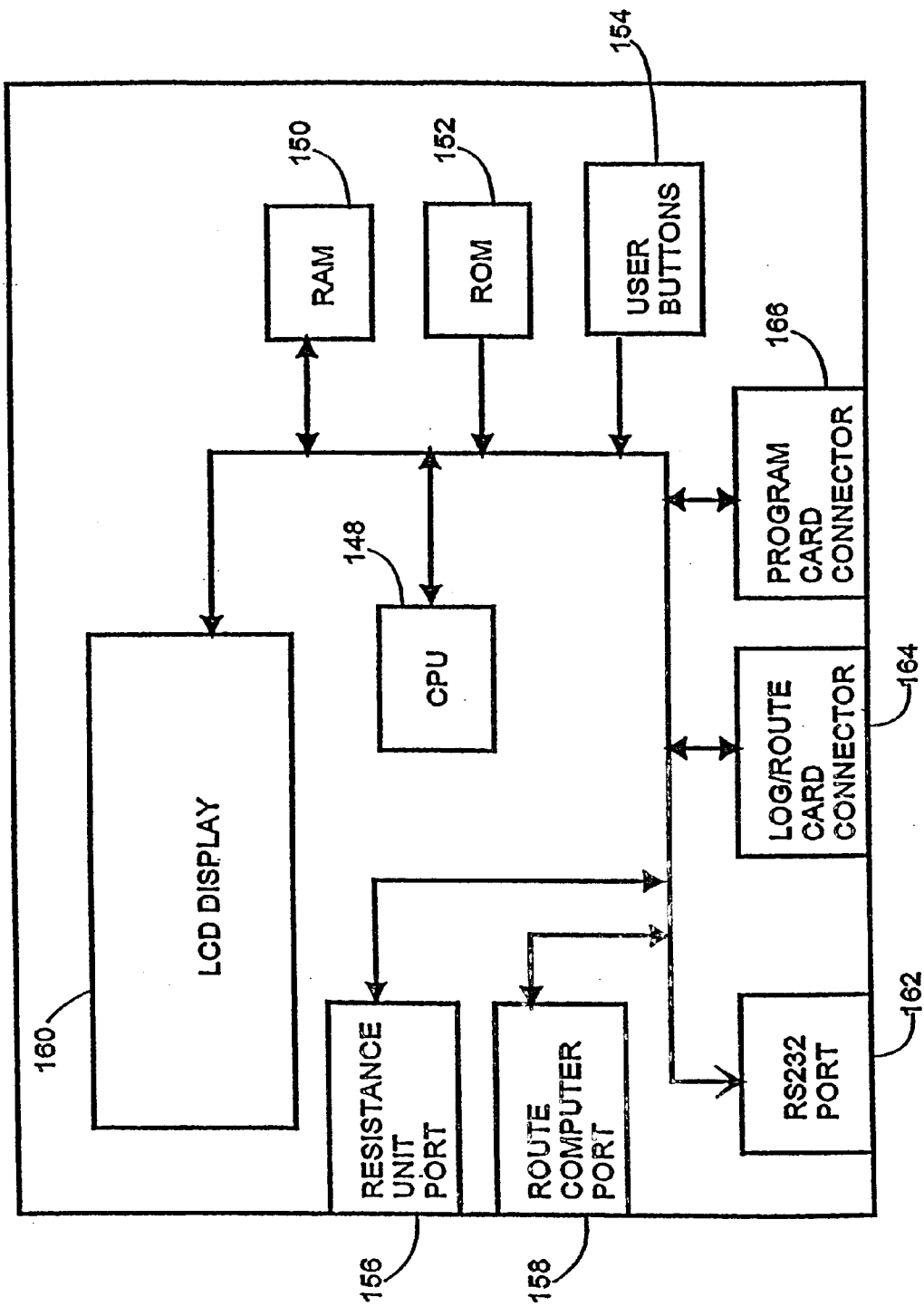

Referring to FIGS. 4a and 4b, once a route has been traveled, and the user docks bicycle 114 into electronic exercise system 100 (for example, at home), a flying lead 146 from base controller 104 couples to base controller port 142 of route computer 108. Route and statistical information can then be downloaded into base controller 104, providing a time-sampled readout of the entire route, including any of: recorded heart rate, inclination, speed, and cadence, and other information, sampled at selected time intervals. Base controller 104 includes a micro controller CPU 148, RAM 150 for storing temporary information for routes, workouts, exercises, and tests, ROM 152 for storing permanent program and data information, user buttons 154 for navigating through menus and selecting options, resistance unit port 156 for coupling via connector 118 to resistance unit 102, route computer port 158 for coupling via flying lead 146 to route computer 108, LCD display 160 for displaying program, statistical, and exercise information to the user, RS232 port 162, and log/route card connector 164 and program card connector 166, both of which accept external memory card devices.

User buttons 154 include a four-direction button pad 154a that allows a user to negotiate forward and backwards through menus, and up and down through menu selections within menu, in an intuitive manner. Enter button 154b selects options, undo button 154c undoes selections, start/pause button 154d starts or pauses base controller operation, and power button 154e turns base controller on and off. Any other convenient arrangement of buttons can be used.

RS232 port 162 allows one base controller 104 to couple with another, either directly, or via a personal computer serial port, modem link, Internet link, and the like. In this manner, two or more users can run the same "virtual" race, even separated by large distances, allowing for mutual training or competitions among bicycle enthusiasts without requiring travel outside of their homes.

Log/route card connector 164 accepts external memory devices, including a read/writable user information and a training log card that allows a user to keep a semi-permanent record of past exercises, routes, and training results. Log/route card connector 164 can also accept a route recording card for capturing and storing a particular route downloaded from the docked route computer 108, or for accepting prerecorded routes that are programmed with the sampled inclination and distances of any route in the world (e.g., the Tour de France) allowing a home user to fully experience and train with those routes. Program card connector 166 accepts similar external memory devices that provide program upgrades to base controller 104. Program upgrades can be made in several ways. A program card can override (completely or in part) the built-in programming of base controller 104. Or a program card's upgrade software can be downloaded into base controller 104 and stored in a persistent memory area (not shown), altering operation of base controller 104, even after removal of the program card. Other types of memory devices can be employed, such as tape back-ups, removable disk drives, and optical disk drives.

Base controller 104 controls resistance unit 102 so as to duplicate either a route recorded by route computer 108 or a programmed route provided from memory or from calculations (which is described further below). By controlling resistance unit 102 over time, a particular route or athletic experience can be closely simulated, including inclination (simulating climbing and descending hills along a route), rolling resistance, aerodynamic drag and forces arising from a rider's acceleration and deceleration. In particular, base controller 102 can increase the forces provided by resistance unit 102 to closely match the resistance presented to a user at a particular position along a route, based upon the local sampled inclination (and/or wind resistance, water resistance (for swimming), steepness (for climbing), etc.).

Figure 5:
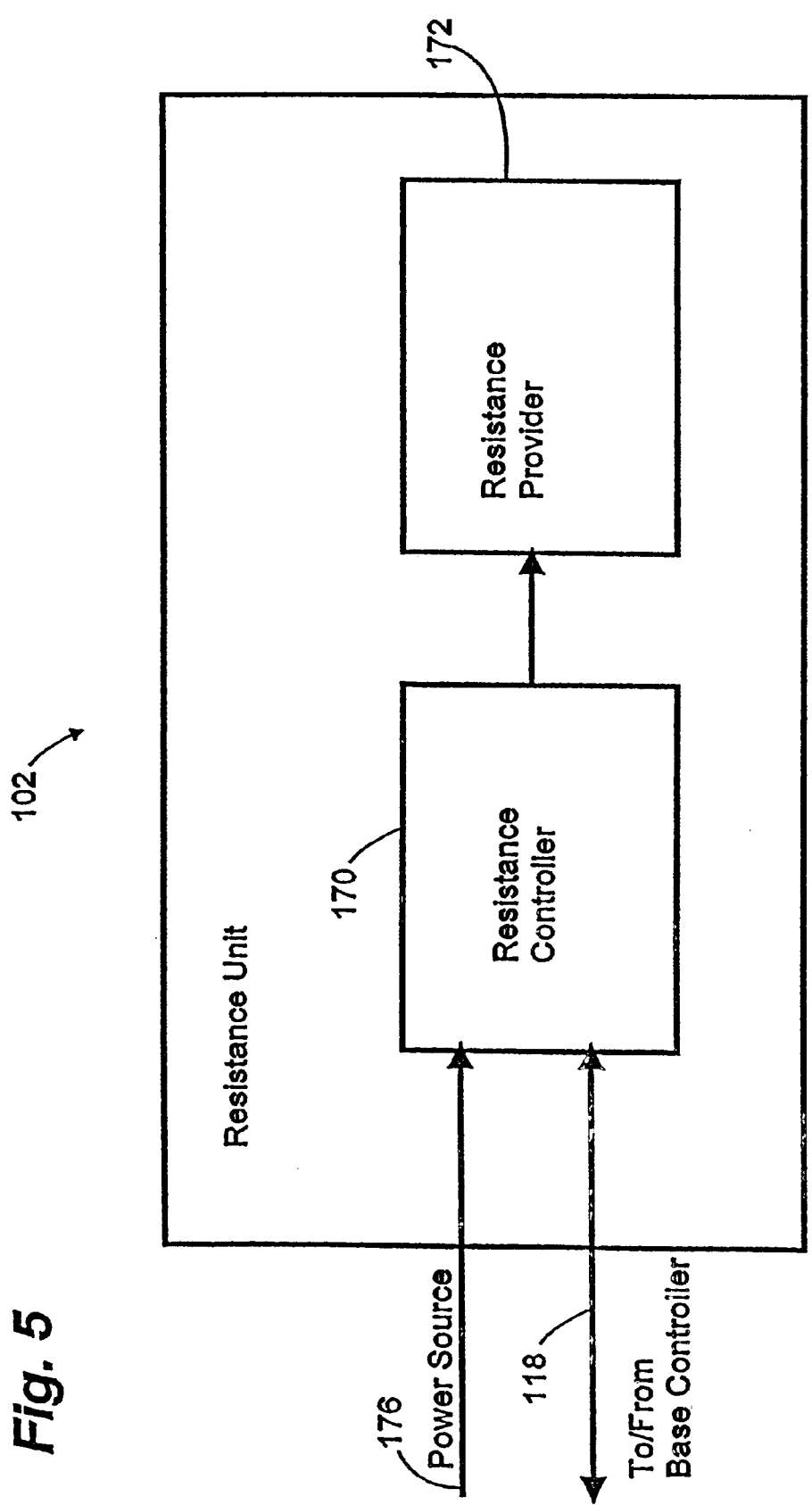
FIG. 5 is a schematic representation of a resistance unit.

Referring to FIG. 5, resistance unit 102 includes resistance controller 170 (which may include a microprocessor system) and resistance provider 172. Base controller 104 can control resistance unit 102 via pulse-width-modulated signals, or with a direct DC signal. Connector 118 couples resistance unit 102 with base controller 104, and also allows resistance unit 102 to provide power received via power cable 176 (from an AC power adapter) to base controller 104. Resistance provider 172 can also implement temperature compensation to account for torque drift caused by varying ambient or induced temperatures, by using a temperature feedback control. Also, a torque sensor (not shown) can measure the torque output of resistance provider 172, and, via a feedback loop to resistance controller 170, control the resistance output of resistance unit 170.

Figure 6:
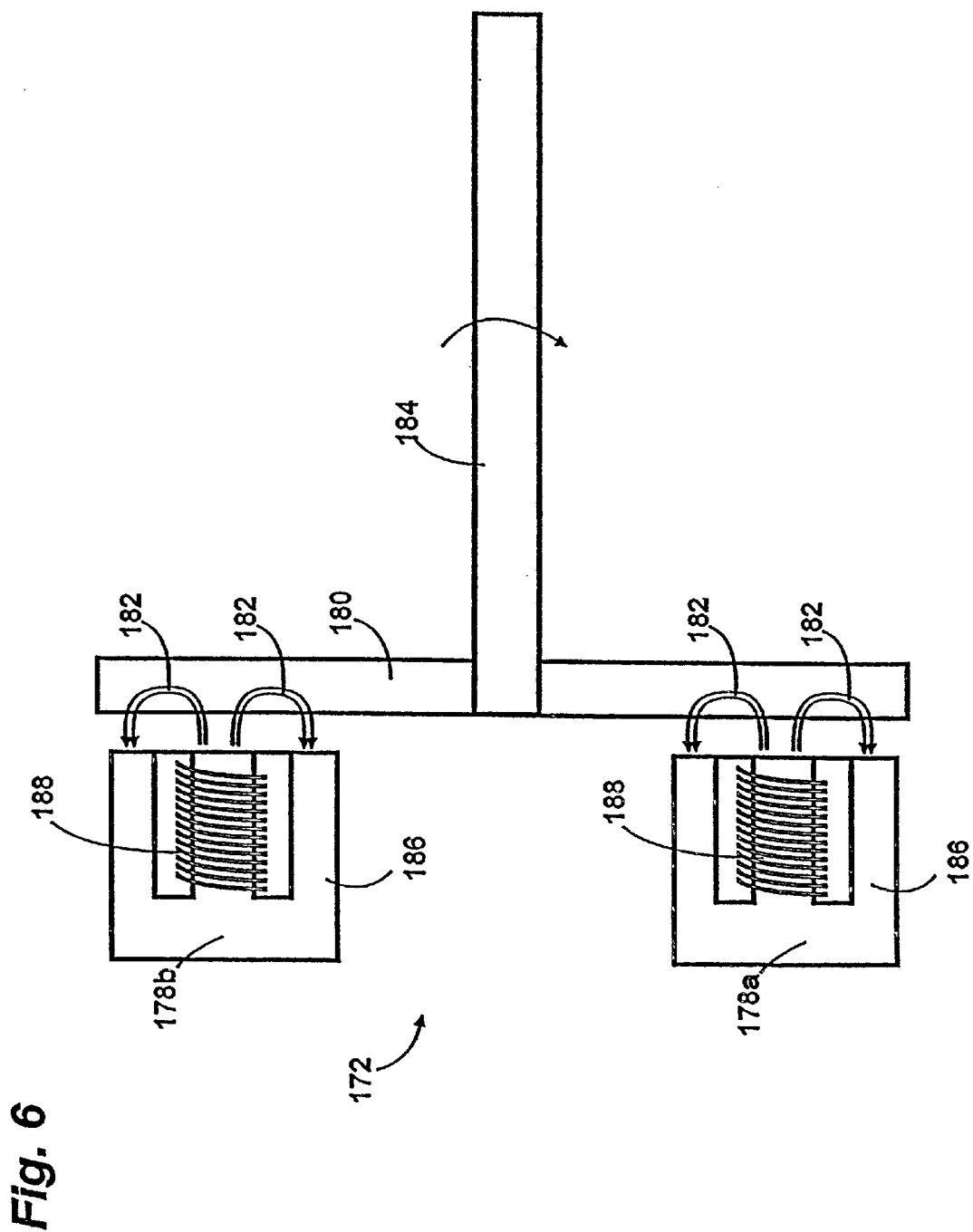
FIG. 6 is a cross-sectional view of an eddy current brake employed in a resistance unit.
Figure 7B:
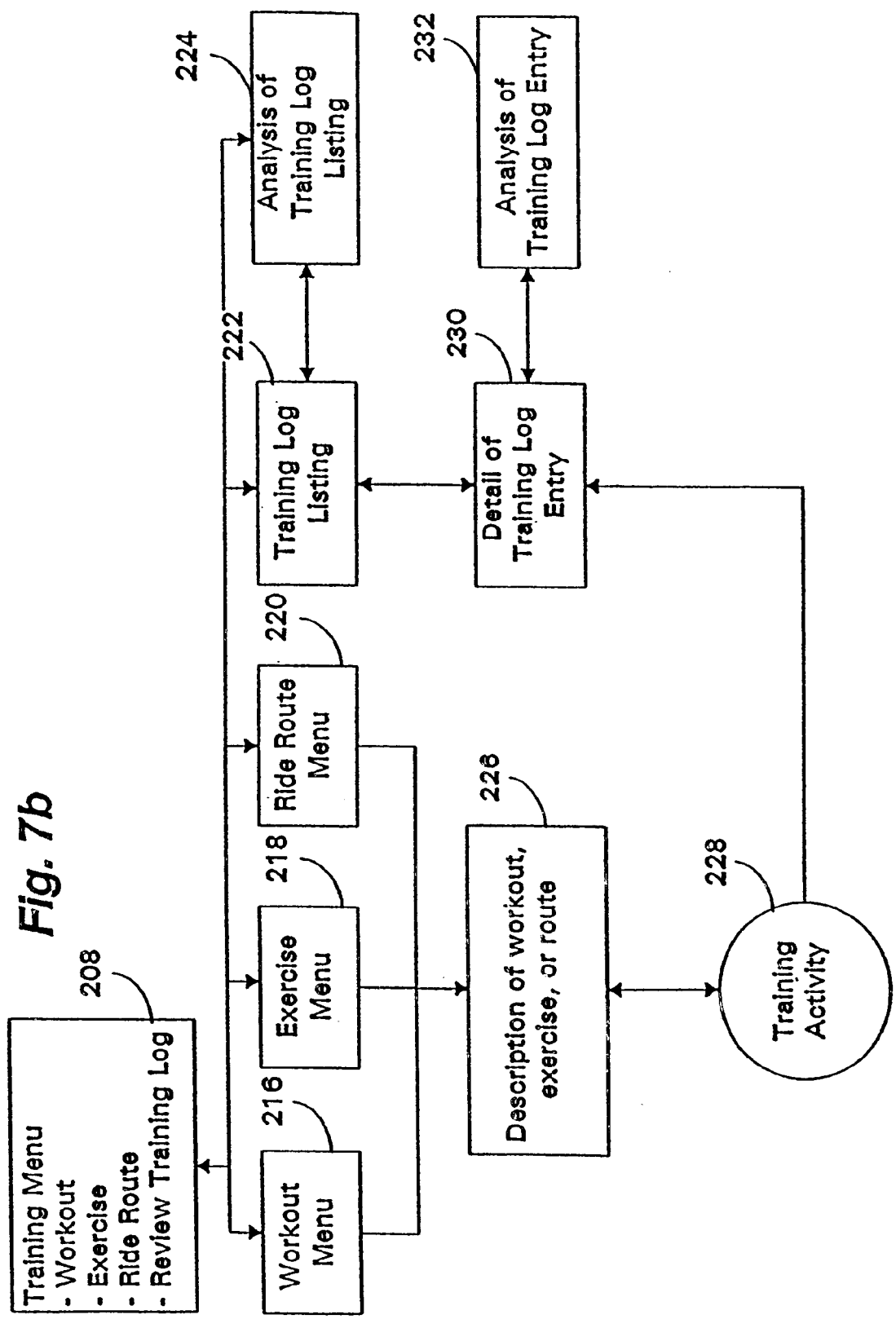
Figure 7C:
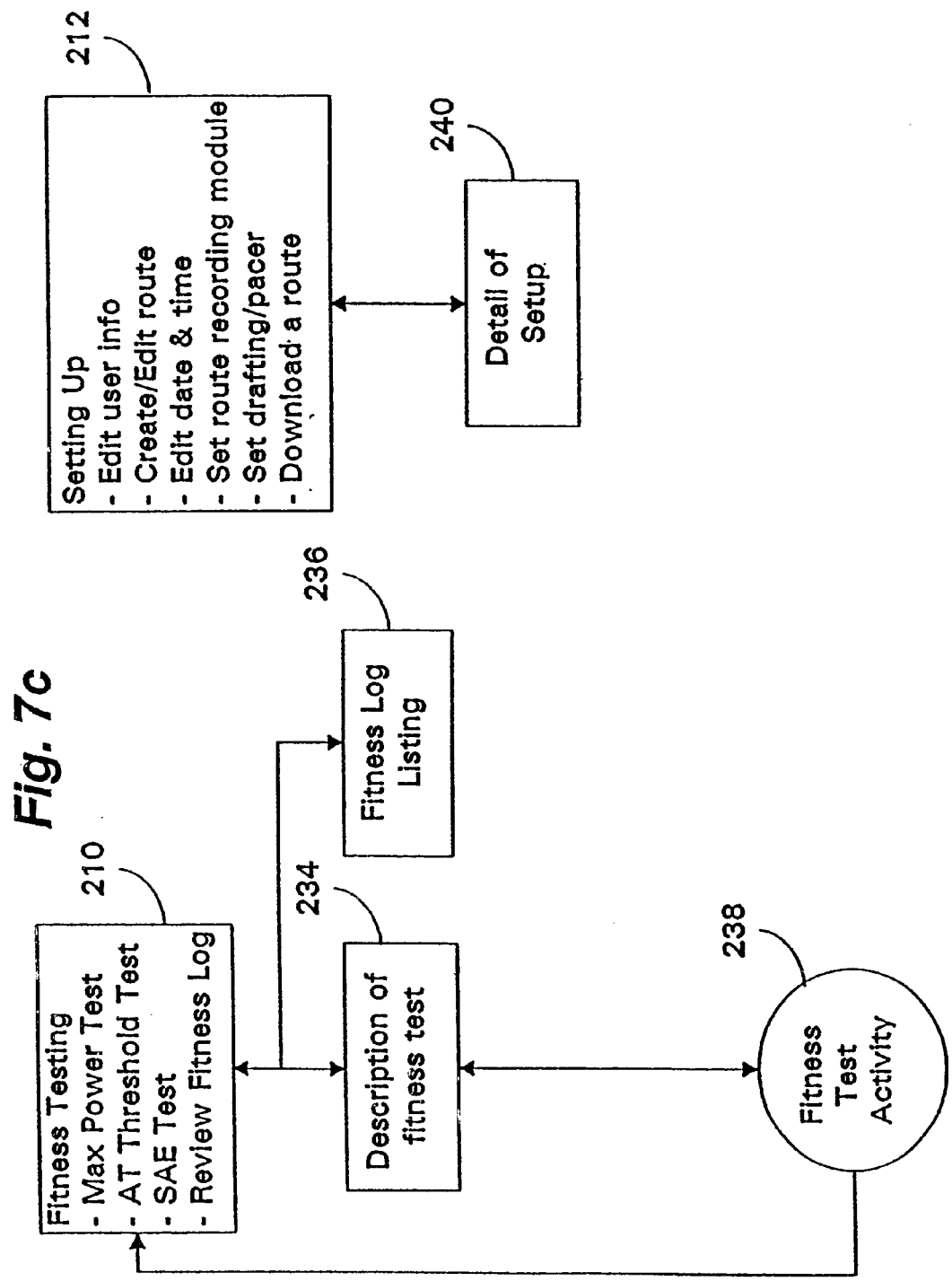
Figure 8A:
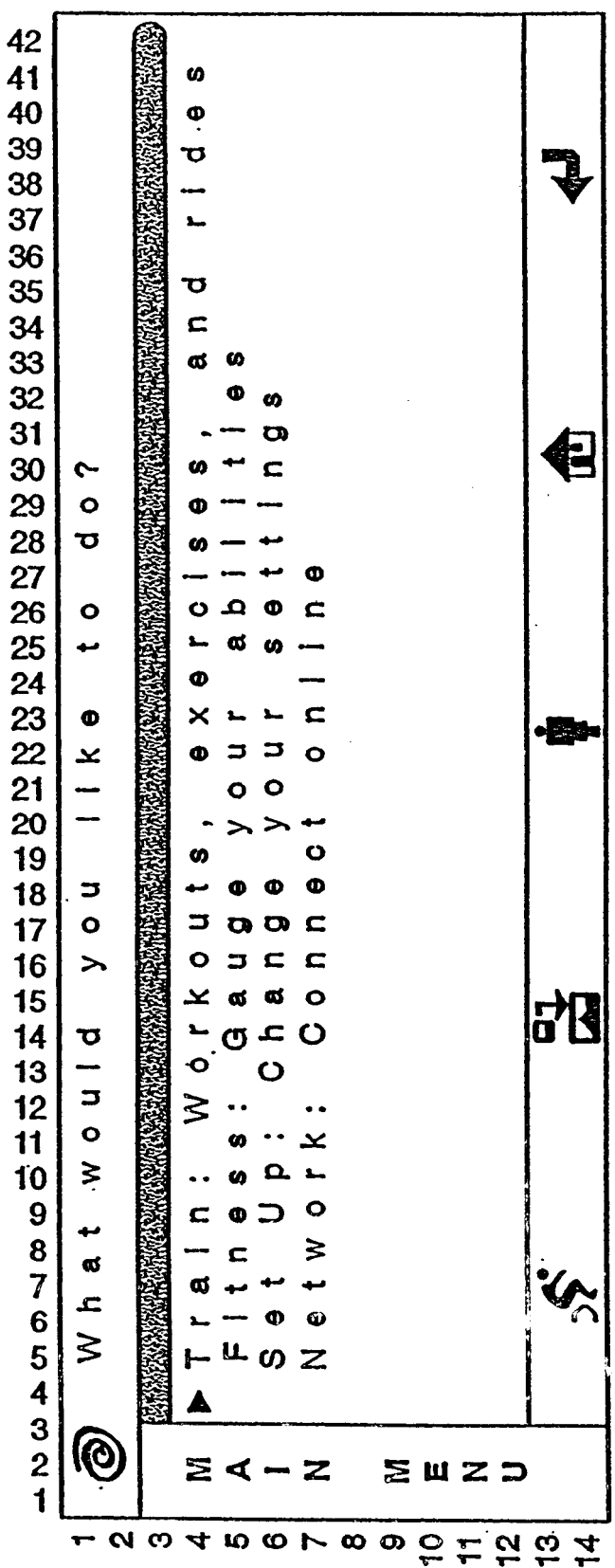
Figure 8D:
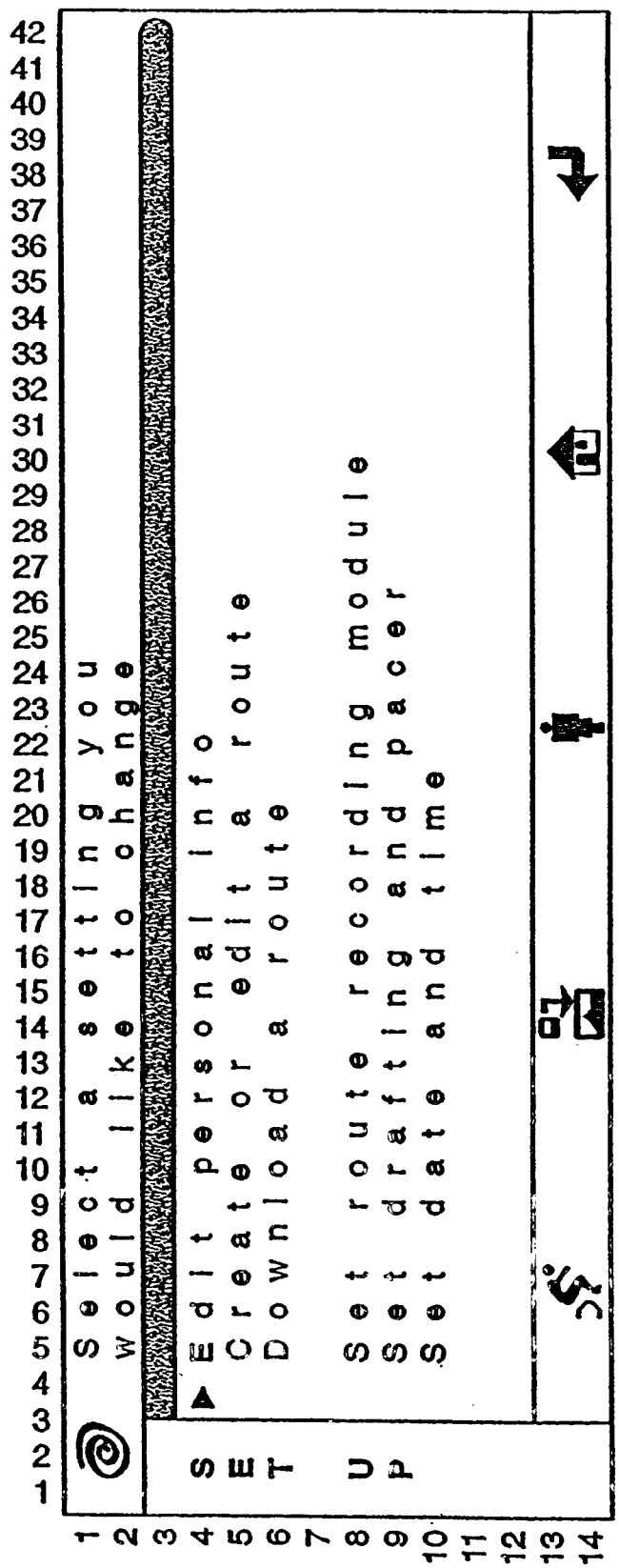
Figure 8E:
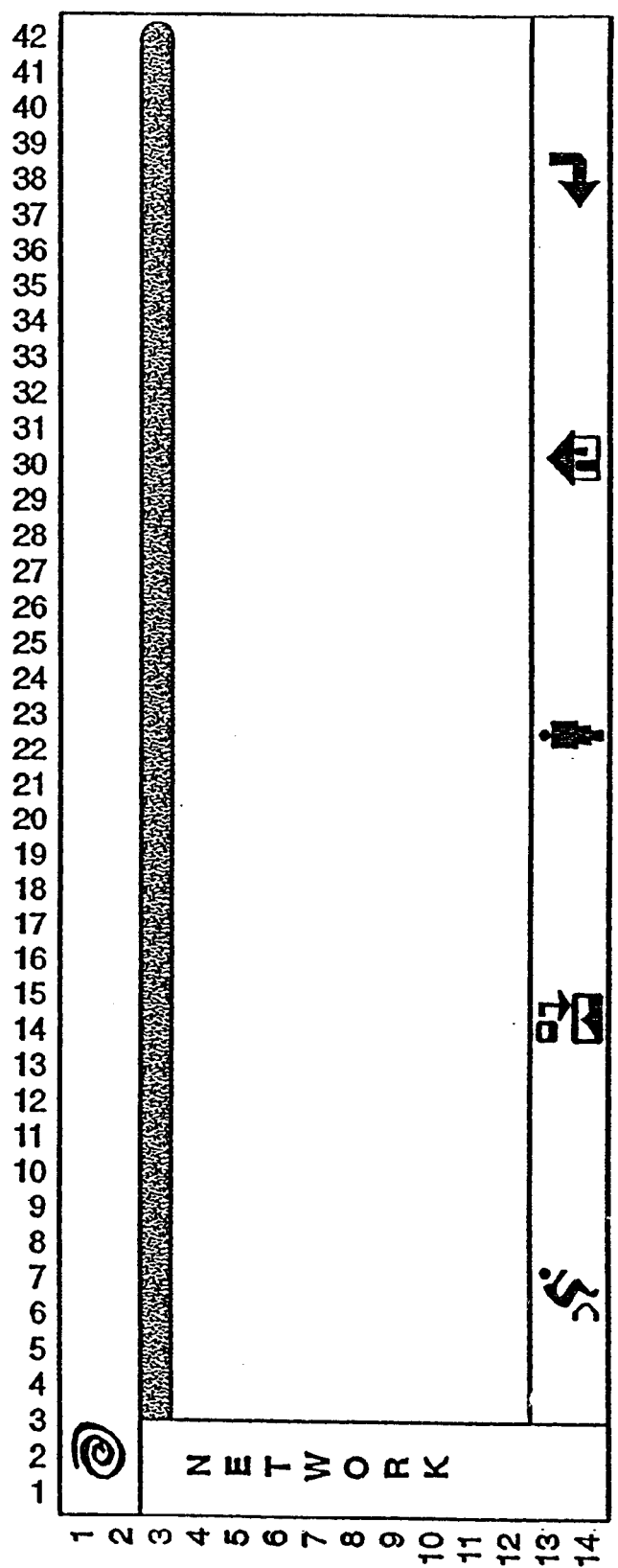

Referring to FIG. 6, one resistance provider 172 employs an eddy current brake. The eddy current brake includes one or more electromagnets 178 (shown in cross-section) coupled in the vicinity of a rotating disk 180, which acts as a conductor to support induced eddy currents. As rotating disk 180 moves through graduated magnetic fields 182 produced by electromagnets 178, the induced eddy currents interact with the magnetic fields to provide a retarding or breaking function on rotating disk 180. Axle 184 of rotating disk 180 is then coupled to the rear tire 112 of bicycle 114, and typically to a flywheel (not shown, e.g., a weighted flywheel or other device (including electrical devices) that conserves or adds angular momentum). Electromagnets 178 preferably employ annular exterior regions 186 surrounding an interior electromagnet post 188 having coiled wires. Annular exterior regions 186 serve to direct magnetic flux flowing from electromagnetic post 188, through rotating disk 180, and then back into electromagnetic post 188, increasing electrodynamic efficiency. Other resistance providers 172 can be used, including controllable fluid resistance elements, electromagnetic motors, magnetic particle brakes, magnetic (smart) fluid resistance elements, hysteresis brakes, and electrical regeneration (where a generator is used across a variable current source, providing required torque).

Referring to FIGS. 4a and 7a through 7c, base controller 104 begins an exercise session 200 with an introduction display 202 on LCD display 160. If the user has never used electronic exercise system 100 before, a getting started screen 204 is shown, with introductory information. Next, main menu 206 presents a number of available options, including training, fitness testing, setting up, and network mode. The user uses button pad 154a to navigate up and down these selections, and enter button 154b to select. Examples of LCD displays for some of these menus are shown in FIGS. 8a through 8d.

If training is selected, training menu 208 is displayed with a number of selections, including (FIG. 7b) workout menu 216, exercise menu 218, ride route menu 220, training log listing 222, and an analysis of the training log listing 224. A workout is a protocol for a single day's exercises, which can be performed either on the full electronic exercise system 100 or outside on the bicycle (or equivalent independent exercise device or technique (e.g., on a treadmill vs. outdoor running)). An exercise is a particular activity designed to train particular athletic skills or performance such as improving peak output, or endurance. A ride route is a particular route (either self-created, via recording with route computer 108, or preprogrammed within base controller 104 or obtained via an external memory device through connector 164). Route is meant to encompass any particular period and/or course of athletic activity, such as climbing up a rock face, running a race track, bicycling along a race course, or swimming a particular route (including back-and-forth laps in a pool), and the like. A user is then given further descriptions 226 of a particular selected workout, exercise, or route, and upon selection, the particular training activity 228 begins.

Base controller 104 creates and updates a user's training log automatically (storing it in a user log external memory). Training log listing 222 allows a user to scroll through the accumulated information to examine a detailed listing 230 of a particular training log entry. Further analysis of a user's training log 224, and a training log entry 232 provide any of a number of useful statistics, including the following: total mileage, weekly mileage vs. time, test scores vs. time, weekly caloric output vs. time, average speed vs. time, power output and heart rate vs. time, % of each heart rate zone vs. time (which can also be accumulated over an entire exercise program), and time distributions for each heart rate zone for a particular period of exercise.

If fitness testing 210 is selected, a number of particular tests can be chosen, including a maximum power test, an aerobic threshold (or lactate threshold power or LTP) test, and a sub-aerobic economy (SAE) test (how long a user can endure exertions just below lactate threshold). Descriptions of a particular test are available (step 234), and then the fitness test activity begins (step 238). The user can choose to examine past test results in their fitness log 236.

Setup menu 212 allows a user to enter and edit information for creating and editing routes, setting dates and time, creating drafting and pacing (to provide virtual exercise and competition partners for an activity), downloading a particular route from either a user-recorded or pre-recorded card memory, and setting route recording resolution (for example, the data sampling rate per wheel revolution for route computer 108). For each selection, the detail 240 of the setup is then shown.

Network mode menu 214 allows a user to select a number of networking modes, including multiuser competitions by direct link, or via a computer modem, Internet link or the like. Linked users can share statistics and performance information, and compete by racing the same virtual course during the same time or different times.

Electronic exercise system 100 allows efficient and accurate standardized fitness tests to determine a user's current fitness level. Many tests require a user to output a constant amount of power for a given duration (for example, the aerobic threshold ratchets up the required power until exhaustion). However, maintaining constant power is not intuitively easy for a user to accomplish. Base controller 104 can instead control resistance unit 102 to provide a specific power output by varying the force applied to rear wheel 112, requiring that the user only maintain a velocity(ies) above some threshold (which can be visually cued via LCD display 160), so that the system automatically adjusts the torque to compensate for user velocity variations while providing a constant power output. Furthermore, route computer 108 docked with base controller 104 allows ready access to heart and RPM/cadence data from the user engaging in a particular fitness test.

Electronic exercise system 100 allows a user to be prescribed a series of workouts that span a length of time (e.g., months) to help the user achieve fitness goals. Periodic fitness tests performed and stored by base controller 104 allow easy evaluation of progress, and allows the test results to alter both the type and intensity of scheduled workouts to steadily achieve the user's fitness targets (e.g., to improve competitiveness in one or more activities, such as triathlon racing, road racing, mountain bike racing, general fitness, sprinting, hill-climbing). The result is a series of workouts that approximate a personal coach while requiring minimal thought input from the user.

In electronic exercise system 100, an exercise "track" is a series of workouts performed to reach a fitness target. A track "lane" is a subdivision of a track: a user is placed within a lane based upon the results of fitness tests. A track may have, e.g., eight lanes (explained further below). A track "level" is a subdivision of a lane: a user is placed within a lane based upon some combination of test scores and personal attributes (such as age, sex, height, weight, and bicycle weight, for example).

With a fitness goal in mind, a user can select an appropriate track for both goal and duration. The base controller 104 can include one or more tracks built in (e.g., for mountain biking, road racing, or triathlon), and more tracks can be added or personalized. Once a user selects a track, the user is prompted to engage in a series of three fitness tests (AT, SAE and maximum power) to evaluate their fitness level. Once the user completes the tests, the user's fitness level is established, and a sequence of workouts are set (until the next testing cycle).

Each track can include periodic retesting days on which the user is required to take the fitness tests again, and update their fitness level. Results of the tests can adjust the user to a different level or lane within the track, and thus alter the workout sequence. Users can also retest themselves as well at any time in addition to the required tests. The user's test history (with dates and scores) is maintained with the user's personal training log for review.

A user (through the above-described menus) can look ahead and review upcoming workouts. Additionally, a user can rearrange the local scheduling of workouts if a conflict arises. Users can be encouraged (with visual prompts) to work outside as often as possible, requiring an on-screen acknowledgment upon completion of the prescribed workout, and downloading of recorded route information from route computer 108 for storage by base controller 104.

The sequence and timing of workouts can be specified by selecting the appropriate lane and level within a track, accomplished automatically. Benchmarks for each of the three fitness tests can be set, and a user's result can be categorized as greater or lesser than each benchmark, so that a user can be placed in one of eight lanes based upon their particular greater/lesser benchmark combination (since there are eight such possible combinations). Any convenient method of dividing up a particular potential user population can be used, to distribute potential results into one or more categories of fitness level. One example of a set of benchmarks includes: a maximum power output of about 350 watts, an LTP threshold of about 200 watts, and an SAE of about 10 minutes.

To place a user at a level within a lane, the quotient of the user's lactate threshold power (LTP) and the user's body weight (BW) (LTP/BW) is compared to 5 ranges, formed by another series of benchmark values. One example of a set of approximate dividing LTP/BW benchmark values (in units of watts/lb.) is (0.6, 1.2, 1.7 and 2.1).

Once a user's lane and level are selected, the workouts are further scaled for duration and intensity by the user's fitness level. For example, a user with an LTP of 100 watts might be required to perform intervals at 80 watts while a user with an LTP of 150 watts might workout at 120 watts. Additional scaling of the duration (length and time) of a workout can be based upon the results of the maximum power and sub-aerobic economy tests.

A track can be conceived as a index to a series of related workouts, combined and stored as a library within base controller 104. Each library entry can include a short and long description and a parameterized prescription of the specific workout, which a user can review.

Another feature of electronic exercise system 100 is that a workout pacer can be calculated and displayed in both visual form as well as numerically (e.g., in terms of speed, power, and distance). The pacer's location for a given workout is based upon the user's own fitness goals, levels, and prescribed workout. For example, for interval-based workouts, the pacer can be a virtual user, experiencing the same forces as the actual user, and outputting constant power. By prescribing power, the force term yields a third order equation in velocity, which the base controller 104 can solve for the pacer's velocity for each upcoming workout interval. The pacer begins each interval with the user, so that if the user performs the interval as prescribed, the user and the pacer will be together throughout the workout. If the user gets ahead of or behind the pacer, the user is riding above or below the recommended level. The solution for the pacer's velocity should be solved compactly enough not to delay the system's control loop. Any convenient numerical solution approach (such as a bisection-style algorithm) can be employed to solve the equation, so long as the solution algorithm fits within each period allowed for by the operations of base controller 104 (and does not spill over into other periods).

Figure 9:
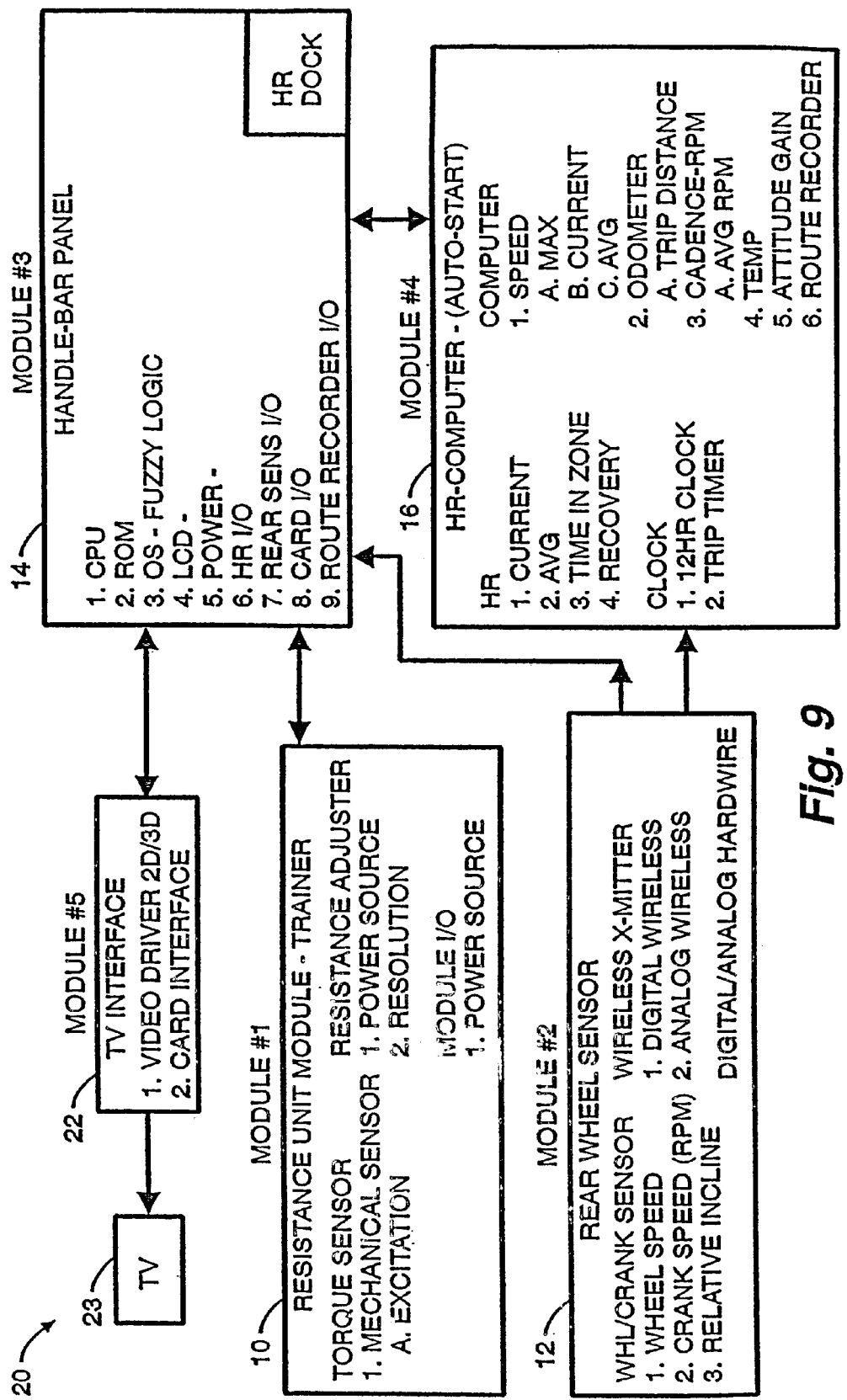
FIG. 9 is a schematic diagram of an electronic exercise system.
Figure 10:
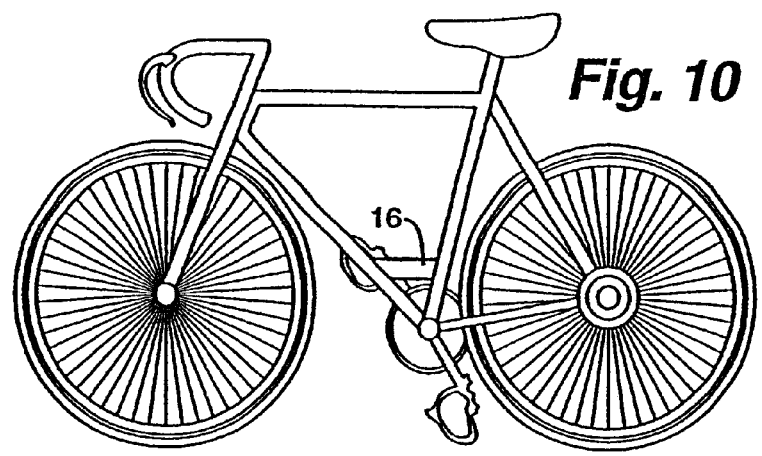
FIG. 10 is a view of a bicycle incorporating features of an electronic exercise system.
Figure 11:
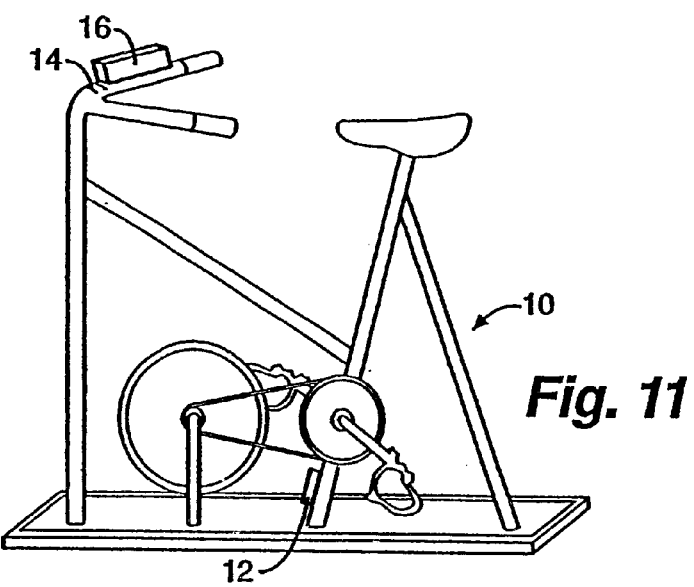
FIG. 11 is a view of a stationary electronic exercise system incorporating a microprocessor controller and interactive display.

Referring to FIG. 9, an embodiment of an electronic trainer 20 includes a resistance unit 22 (e.g., the exercise cycle 10 shown in FIG. 11), a first sensor 12 carried by the cycle 10, a control/interface and display unit 14 carried by the cycle 10 and a portable heart rate/cycle computer 16 (also shown on the bicycle 18 of FIG. 10). The heart rate/cycle computer 16 may take the form of a wrist-watch type cycle computer (not shown, but of the type commercially available) or wireless monitor, but is in either case dockable with the control interface unit 14. The resistance unit 10 is computer or microprocessor controlled and provides a step-less or smooth resistance via its electronic control mechanism 14. The variable resistance may be provided by a suitable resistance mechanism such as an eddy current brake (preferred), but friction, fan load type, other resistance mechanisms may be used as well. It uses onboard electronics and may incorporate a rechargeable power source. It can enable the calculation and graphical display of operational parameters and performance levels of the user, such as user stroke efficiency, through sampling performance criteria such as user generated instantaneous torque output.

The first sensor 12 can be mounted on the resistance unit and can be a wire or wireless rpm, speed and incline sensor. It provides wire or wireless input and output transmission of rpm or cadence relative incline and wheel RPM to the control interface unit 14 and/or the cycle computer 16.

The control/interface unit 14 of the present invention can be semi-permanently mounted upon the resistance unit 10, and used indoors. The control/interface unit provides an LCD interface 22 for display of basic function status and a workout profile. Control/interface unit 14 may include fuzzy logic control for the resistance unit based on one or more of the following criteria: heart rate, user torque output, speed, incline, a ROM resident profile, an external data input profile (EEPROM, PCMCIA or like card reader), user recorded profile from remote site or field data (transferred or downloaded from the wrist type cycle computer) and/or a user created profile of an exercise regime or particular race course or program of exercise. Control/interface unit 14 includes an IEEE 1394 hardware interface input/output port or the like.

Portable cycle computer and monitor 16 may be constructed from a commonly known wrist-watch type computer, often worn by and used to monitor heart rate of bicyclists, runners and like. Or, as above, it can be mounted on the bicycle, and monitor a user's heart rate remotely. It may be wireless. Preferably it should be water resistant. Cycle computer and monitor 16 can monitor and store one or more of the following: average heart rate, current heart rate, high/low target zones with alarm feature, heart rate recovery, ECG accurate, heart rate sampling and time in/out of target zone. Other measuring and recording functions for assessing an exerciser's condition might include $CO^2$, $O^2$ or other blood gas levels, respiration rate and the like. Cycle computer and monitor 16 may also provide other functions such as: route recording, current speed, average speed, maximum speed, current grade or incline, accumulated altitude, trip distance, an odometer function, cadence or rpm storage, and an automatic start/stop.

With respect to the route recording or mapping feature, the portable, dockable cycle computer and monitor 16 may either automatically or manually sample incline, distance and heart rate at selected intervals during an outdoor workout or race, recording the same. The incline or angle sensor can be a dampened pendulum moving a potentiometer with the voltage input to an analog-to-digital converter. A global position satellite (GPS) function may be included as may a yaw sensor for providing orientation information, and an air flow sensor for providing information about relative air speed.

The cycle computer and monitor 16 also may include typical clock or timing functions such as a stopwatch feature, lap timer, interval timer and time of day and alarm.

The programmable control/interface unit 10 can be programmed to have a variety of tracks, i.e., digital structure(s) for providing a workout or series of workouts of varying intensity. For example, one track may be a "marathon" track, another may be a "1500 m" track. Other tracks may be designed or written to improve the cardiovascular fitness level, to strengthen or emphasize certain muscle groups, and then loaded into programmable control/interface unit 10 as an upgrade. A user may select a track or a series of tracks to progress toward a desired fitness goal, or the program may be written to make the selection based on fitness test results. For a user, the characteristics of the selected track may be determined by the user's ultimate goal and a fitness test(s). The test results dictate a work plan or program for progressive improvement to reach the selected goal or to maintain a selected level of fitness. When the test results are entered, the control/interface unit 10 correlates fitness level with available preprogrammed (memorized) or customized workout profiles. The control/interface 14 may automatically control the resistance member 10 depending on a specified fitness level, selected track, and goal. A sophisticated athlete at a fitness level, but with a goal in mind, will be able to customize or design a particular track for his/her own use.

The computer and monitor 16 may include a "reset" button that allows clearing the route recording memory. The computer and monitor 16 also has an "LED" (or similar indication) to show the unit is recording route data. The LED can be made to flash at the same time interval that data samples are taken and stored in the cycle computer and monitor 16. The cycle computer and monitor 16 can automatically record heart rate when either in the recording mode or a heart rate watch mode. The user can then download route recorded data into control interface unit 10. This can be displayed as a graph of heart rate related to profile/time/distance information, allowing the user to see what his/her heart rate was at specific times of the recorded race. Cycle computer and monitor 16 can automatically start recording when triggered by a received pulse. In other words, once a heart rate sensor receives a user's pulse signal and the cycle computer and monitor 16 is close enough to receive the signal, the computer and monitor 16 is triggered and starts recording.

The incline sensor may also be damped with alcohol and water to allow for accurate incline sensing at high and low temperatures.

In use, an exerciser carries or wears the cycle computer and monitor 16 during an exercise period which might cover, via bicycle, a selected route. The computer and monitor 16 samples and records parameters such as heart rate, respiration, distance covered, location elapsed time, incline, etc. at selected intervals during the period. The computer and monitor 16, bearing its data, is docked with the control interface unit 14 so the date can be accessed or downloaded for use. In the playback mode, the recorded data is processed and used to automatically set and adjust the resistance of the resistance unit 10 to simulate, for example, climbing hills along the route covered during the exercise period.

Referring to FIG. 13, an embodiment of the invention includes a resistance module 10*b*, a base computer 14*b*, and a portable cycle computer 16*b*. Resistance module 10*b* can be a magnetic brake coupled by an IR transceiver (or other connection) to base computer 14*b*, and may have a micro controller for controlling the resistance provided to a user. Cycle computer 16*b*, similar to that described above, is portable to be worn by the user (or attached to an exercise device) while performing an exercise (such as riding a bicycle outdoors) and then docked with base computer 14*b* to provide stored information for, e.g., duplicating an outdoor course indoors. Base computer 14*b* can accept an external memory card 26 (such as 64K EEPROM card) that can have preset courses, or store user information for later use, or for use on another electronic exercise system 20. Base computer 14*b* can be coupled to other trainers via port 24*b*, and also can display information on an external video monitor or TV 23*b* via adapter 22*b*.

Figure 12:
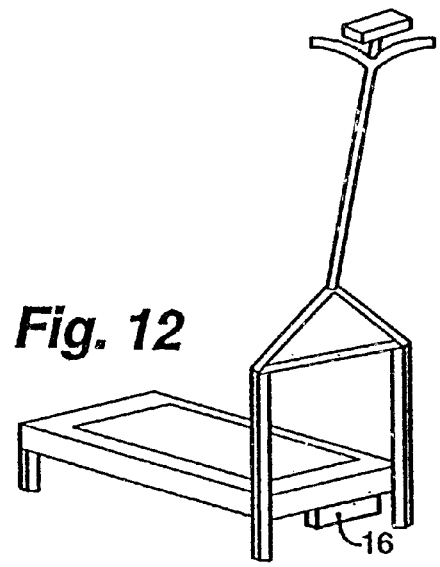
FIG. 12 is a view of an electronic treadmill training/exercise device.

Other embodiments are within the scope of the claims. Features of the various described embodiments may be combined. Although the described embodiments of the present invention employ conventional (or stationary) bicycles, the route mapping and workout replicating concept of the present invention may be adapted for use with other exercise means such as treadmills (FIG. 12), skiers, steppers, dry or wet swimming exercisers, and the like. In each case, a relatively static exercise means can be made to closely duplicate a dynamic one. For example, a rock climber can record distance, altitude, speed, and heart rate for a particular rock face, and duplicate the route on a static exercise device such as a climber. A skier can similarly record distance, air speed, altitude, and heart rate and duplicate a particular route indoors. Runners and swimmers could duplicate particular races with appropriate static resistance devices (for example, treadmills and forced-water lap pools).

What is claimed is:

1. Apparatus comprising:

a physical activity monitor including a sensing and recording arrangement that during a first period of physical activity senses and records data characterizing the physical activity performed by a user; and an exercise device configured to simulate the physical activity, wherein the exercise device has a control and wherein the sensing and recording arrangement of the monitor is separate from the control of the exercise device, wherein the recorded data from the physical activity monitor is supplied to the control of the exercise device, and wherein the control of the exercise device uses the recorded data from the physical activity monitor to control operation of the exercise device and simulate the physical activity of the first period for the user during a second period of physical activity using the exercise device.

2. The apparatus of claim 1 wherein the physical activity monitor measures a first index of physical exertion.

3. The apparatus of claim 2 wherein the first index of physical exertion comprises an index of a distance traveled by the user.

4. The apparatus of claim 2 wherein the first index of physical exertion comprises an index of an inclination of the user.

5. The apparatus of claim 2 wherein the first index of physical exertion comprises an index of a force exerted by the user.

6. The apparatus of claim 2 wherein the first index of physical exertion comprises an index of a heart rate of the user.

7. The apparatus of claim 1 wherein the exercise device control is interconnected with a resistance provider, wherein the exercise device control is operable to control the resistance provider in accordance with the recorded data to simulate the physical activity.

8. The apparatus of claim 1 wherein the physical activity of the user simulated by the exercise device is a non-stationary bicycle ride.

9. The apparatus of claim 1 wherein the physical activity of the user simulated by the exercise device is a non-stationary rock climb.

10. The apparatus of claim 1 wherein the physical activity of the user simulated by the exercise device is a non-stationary swim.

11. The apparatus of claim 1 wherein the physical activity of the user simulated by the exercise device is a non-stationary run.

12. Apparatus comprising:

a physical activity monitor that records sampled data, the data comprising indices of a force exerted by a user and of a distance traveled by the user during a first period of non-stationary physical activity by the user; and a stationary exercise device configured to simulate the physical activity, wherein the stationary exercise device includes a control that uses the recorded data from the physical activity monitor to control operation of the stationary exercise device during a second period of stationary physical activity on the exercise device which simulates the first period of non-stationary physical activity.

13. The apparatus of claim 12 wherein the physical activity comprises a bicycle ride, and wherein the physical activity monitor further comprises a rotational sensor attached to a bicycle used during the non-stationary bicycle ride.

14. The apparatus of claim 12 wherein the physical activity comprises a bicycle ride, and wherein the physical activity monitor further comprises an inclination sensor.

15. The apparatus of claim 12 wherein the physical activity comprises a bicycle ride, and wherein the physical activity monitor further comprises a heart rate sensor coupled to the user.

16. The apparatus of claim 12 wherein the physical activity comprises a bicycle ride, and wherein the stationary exercise device comprises a resistance unit removably coupled to a bicycle; and a controller, the controller adapted to receive the data recorded by the physical activity monitor and to control the resistance unit to simulate the non-stationary bicycle ride.

17. Apparatus comprising:

a physical activity monitor that records sampled data, the data comprising indices of a force exerted by a user and of a distance traveled by the user during a non-stationary bicycle ride by the user occurring during a first time period, the physical activity monitor further comprising a rotational sensor attached to a bicycle used during the non-stationary bicycle ride, an inclination sensor, and a heart rate sensor coupled to the user; and a stationary exercise device that uses the recorded data from the physical activity monitor to simulate the non-stationary bicycle ride during a subsequent second time period of physical activity using the stationary exercise device, the stationary exercise device comprising a resistance unit removably coupled to a bicycle; and a controller, the controller adapted to receive the data recorded by the physical activity monitor and to control the resistance unit to simulate the non-stationary bicycle ride.

18. A method comprising:

during a first period of physical activity in a first environment, recording data characterizing the physical activity performed by a user; and during a second period of physical activity in a second environment which simulates the first environment, using the recorded data to control operating characteristics of the second environment to simulate the physical activity of the first period for the user.

19. The method of claim 18 wherein the recorded data comprises a first index of physical exertion.

20. The method of claim 19 wherein the first index of physical exertion comprises an index of a distance traveled.

21. The method of claim 19 wherein the first index of physical exertion comprises an index of an inclination of a user.

22. The method of claim 19 wherein the first index of physical exertion comprises an index of a force exerted by a user.

23. The method of claim 19 wherein the first index of physical exertion comprises an index of a heart rate of a user.

24. The method of claim 18 wherein the second environment includes a controller that receives the recorded data and controls a resistance provider in accordance with the received data to simulate the physical activity.

25. The method of claim 18 wherein the simulated physical activity of the user is a non-stationary bicycle ride.

26. The method of claim 18 wherein the simulated physical activity of the user is a non-stationary rock climb.

27. The method of claim 18 wherein the simulated physical activity of the user is a non-stationary swim.

28. The method of claim 18 wherein the simulated physical activity of the user is a non-stationary run.

29. A method comprising:

recording sampled data during a first time period, the data comprising indices of a force exerted by a user and of a distance traveled by the user during a non-stationary bicycle ride by the user; and using the recorded data to control operation of a stationary bicycle trainer to simulate characteristics of the non-stationary bicycle ride on the stationary bicycle trainer during a subsequent second period of physical activity on the stationary bicycle trainer.

30. The method of claim 29 wherein the recorded data further comprises data indicative of rotation of a wheel of a bicycle used during the non-stationary bicycle ride.

31. The method of claim 29 wherein the recorded data further comprises data indicative of an inclination of a bicycle used during the non-stationary bicycle ride.

32. The method of claim 29 wherein the recorded data further comprises data indicative of a heart rate of the user.

33. The method of claim 29 wherein a controller receives the recorded data and controls a resistance unit associated with the bicycle trainer to simulate the non-stationary bicycle ride.

34. A method comprising:

recording sampled data in a storage unit, the data comprising indices of a force exerted by a user and of a distance traveled by the user during a non-stationary bicycle ride by the user occurring during a first time period;

interconnecting the storage unit with a stationary bicycle exercise device having a resistance unit; and utilizing the recorded data to control the resistance unit to simulate the non-stationary bicycle ride using the stationary bicycle exercise device during a subsequent second period of physical exercise employing the resistance unit.

* * * * *